United States Patent [19]
Li et al.

[11] Patent Number: 5,715,942
[45] Date of Patent: Feb. 10, 1998

[54] PACKAGE AND HOLDER FOR SUTURE ANCHOR WITH SUTURES AND SURGICAL NEEDLES ATTACKED

[75] Inventors: Lehmann K. Li, Milford; Stephen A. Maguire, Huntington; Joseph D. Kachala, Shelton, all of Conn.

[73] Assignee: Li Medical Technologies, Inc., Shelton, Conn.

[21] Appl. No.: 751,116

[22] Filed: Nov. 15, 1996

[51] Int. Cl.$^6$ .................................................. A61B 17/06
[52] U.S. Cl. .................................. 206/339; 206/63.3
[58] Field of Search .............................. 206/363, 370, 206/438, 63.3, 564, 339, 345, 346, 347, 338

[56] References Cited

U.S. PATENT DOCUMENTS

| | | |
|---|---|---|
| 4,053,280 | 10/1977 | Salisbury .................. 206/363 |
| 4,089,409 | 5/1978 | Cerwin . |
| 4,126,221 | 11/1978 | Cerwin . |
| 4,762,688 | 8/1988 | Berry, Jr. ............... 206/363 X |
| 4,946,468 | 8/1990 | Li . |
| 5,002,550 | 3/1991 | Li . |
| 5,078,730 | 1/1992 | Li et al. . |
| 5,084,058 | 1/1992 | Li . |
| 5,087,263 | 2/1992 | Li . |
| 5,133,723 | 7/1992 | Li et al. . |
| 5,163,946 | 11/1992 | Li . |
| 5,174,087 | 12/1992 | Bruno . |
| 5,176,682 | 1/1993 | Chow . |
| 5,312,422 | 5/1994 | Trott . |
| 5,314,433 | 5/1994 | Li . |
| 5,318,577 | 6/1994 | Li . |
| 5,354,298 | 10/1994 | Lee et al. . |
| 5,372,599 | 12/1994 | Martins . |

*Primary Examiner*—Jacob K. Ackun
*Attorney, Agent, or Firm*—Ostrolenk, Faber, Gerb & Soffen LLP

[57] ABSTRACT

A holder for a suture anchor having a suture coupled to the suture anchor and at least one suture needle attached to the suture, the holder comprising a planar member of generally rectangular shape having a cutout at each corner of the member about which sutures can be wound, the member having at least one channel formed therein for receiving the surgical needle and a receptacle formed therein for receiving the suture anchor, and further comprising a channel formed in the member for frictionally engaging the suture at a point along the length of the suture close to the suture anchor, thereby allowing the suture anchor to be removed from the holder without causing the suture to unwind from the holder.

47 Claims, 3 Drawing Sheets

PACKAGE AND HOLDER FOR SUTURE ANCHOR WITH SUTURES AND SURGICAL NEEDLES ATTACKED

BACKGROUND OF THE INVENTION

The present invention relates to surgical anchors and fasteners, and in particular, to a surgical anchor for fastening sutures into bio-organic material, for example, bone. Even more particularly, the present invention relates to a sterile package and holder for a suture anchor with sutures attached. Preferably, the sutures also have attached thereto, in addition to the suture anchor, the suture needles.

U.S. Pat. No. 5,078,730 to Li et al. discloses a holder for a suture anchor assembly. The holder of U.S. Pat. No. 5,078,730 comprises a generally rectangular body of material having its outer surfaces cut away in various locations so as to form suture anchor holding means for releasibly holding a suture anchor to the holder, suture holding means for releasibly holding a suture to the holder and needle holding means for releasibly holding a pair of surgical needles to the holder. The suture anchor holding means, suture holding means and needle holding means comprise channels formed in the outer surfaces of the body to the profiles of the particular suture anchor assembly members they are to receive. The holder of U.S. Pat. No. 5,078,730 includes a number of islands formed in an archipelago type pattern about which the sutures are wound.

A problem arises with the suture anchor assembly holder of U.S. Pat. No. 5,078,730 in that a complicated design is necessary employing an archipelago type pattern structure and a cover to press towards the side surfaces of the holder and thereby provide some resistance to the passage of the suture through the space between the covered portions and the side surfaces. This resistance is necessary to control the release of the suture from the holder. Without these covers, the suture would freely release from the holder once the suture anchor is removed, thereby causing problems, such as entanglement and possibly contamination of the suture at the surgical site.

It is important that the suture be controllably released from the suture holder in order to minimize installation problems.

SUMMARY OF THE INVENTION

It is an object of the present invention to provide a package for a suture anchor including sutures and suture needles attached thereto.

It is a further object of the present invention to provide a holder for a suture anchor with sutures and suture needles attached thereto.

Yet still another object of the present invention is to provide a simplified holder for a suture anchor with sutures and suture needles attached thereto.

Yet still a further object of the present invention is to provide a holder for a suture anchor with sutures and suture needles attached thereto which provides for controllable release of the sutures, thereby preventing entanglement and contamination of the sutures.

It is yet still a further object of the present invention to provide a holder for a suture anchor with sutures and suture needles attached thereto which provides a safe and sterile means for holding the suture anchor, sutures and suture needles.

The above and other objects of the present invention are achieved by a holder for a suture anchor having a suture coupled to the suture anchor and at least one suture needle attached to the suture, the holder comprising a planar member of generally rectangular shape having a cutout at each corner of the member about which the suture can be wound, the member having at least one channel formed therein for receiving the surgical needle and a receptacle formed therein for receiving the suture anchor, and further comprising a channel formed in the member for frictionally engaging the suture at a point along the length of the suture close to the suture anchor, thereby allowing the suture anchor to be removed from the holder without causing the suture to unwind from the holder.

According to the invention, the cutouts and channels are exposed and a cover is not employed over the planar member.

The above and other objects are also achieved by a package for a holder for a suture anchor having a suture coupled to the suture anchor and at least one suture needle attached to the suture, the package comprising: a planar member of generally rectangular shape having a cutout at each corner of the member about which the suture is wound, the member having at least one channel formed therein for receiving the surgical needle and a receptacle formed therein for receiving the suture anchor, and further comprising a channel formed in the member for frictionally engaging the suture at a point along the length of the suture close to the suture anchor, thereby allowing the suture anchor to be removed from the holder without causing the suture to unwind from the holder, a suture anchor in the receptacle, a suture coupled to the suture anchor and wound about the holder, a surgical needle coupled to the suture and disposed in the channel; and a pouch receiving the holder with the suture anchor, suture and surgical needle disposed thereon.

The above and other objects of the invention are further achieved by a holder for a suture anchor having a suture coupled to the suture anchor and at least one suture needle attached to the suture, the holder comprising: a member having a surface having a substantially planar portion having a cutout at each corner of the member about which the suture can be wound, the member having at least one channel formed therein for receiving the surgical needle and a receptacle formed therein for receiving the suture anchor, and further wherein the suture is frictionally engaged by the holder at a point along the length of the suture close to the suture anchor, thereby allowing the suture anchor to be removed from the holder without causing the suture to unwind from the holder, the cutouts and receptacle for the suture anchor being exposed and a cover not being disposed over the member The above and other objects of the invention are also achieved by a holder for a suture anchor having a suture coupled to the suture anchor and at least one suture needle attached to the suture, the holder comprising: a member having a surface having a substantially planar portion having a cutout at each corner of the member about which the suture can be wound, the member having at least one channel formed therein for receiving the surgical needle and a receptacle formed therein for receiving the suture anchor and further wherein the suture is wound about at least one side of the member between the cutouts of the member.

Other features and advantages of the present invention will become apparent from the detailed description which follows.

BRIEF DESCRIPTION OF THE DRAWINGS

The invention will now be described in greater detail in the following detailed description with reference to the drawings in which.

DETAILED DESCRIPTION OF EMBODIMENTS OF THE INVENTION

Figure 7:
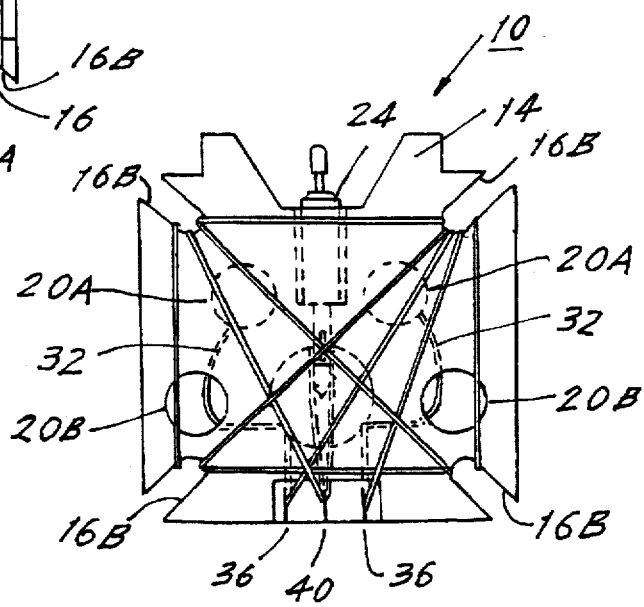
FIG. 7 is a back plan view of the holder.

With reference now to the drawings, the holder according to the present invention comprises a holder assembly generally indicated at 10. The holder assembly preferably comprises a generally square first member 12 adhesively fastened to a second member 14. The members 12 and 14 preferably are generally rectangular or square in shape with a plurality of cutouts 16 provided at each corner. The members 12 and 14 may have any other suitable shape. Preferably, the members 12 and 14 comprise a foam plastic, for example, a medical grade polyurethane foam. Member 12 is sized such that its thickness is the same as or somewhat larger than the thickness of the surgical anchor which is to be received in the holder. Member 14 comprises a thin layer, compared to the member 12, adhesively fastened to the member 12. The member 14 preferably is sized somewhat larger than member 12, as shown, so that the adhesive used to secure member 14 to member 12 will not contact the suture to be wound on the members. The members 12 and 14 are of light weight, relatively soft and have a number of additional cutouts in the members 12 and 14 formed therein. These cutouts include a cutout 18, only in the member 12, for the anchor itself, and a number of circular cutouts 20 for the surgical needles. Cutouts 20 are connected by channels 22 formed in the foam material 12. In the preferred embodiment, cutouts 20A are formed only in member 12 with cutouts 20B extending through both members 12 and 14. See FIG. 7. This facilitates removal of surgical needles 32. Also, cutouts 16 may each comprise a cutout 16A in member 12 and a smaller cutout 16B in member 14.

Although the holder assembly shown is made of two members 12 and 14 adhesively glued together, the holder assembly may be made of one piece. Making the holder assembly in two pieces 12 and 14 eases some manufacturing processes because as will be discussed below, some of the recesses and cutouts in the holder assembly are through-holes whereas others are pockets, with the bottom of the pocket being formed by member 14. For example, cutouts 18, 20A and 38 (FIG. 2) are pockets (bottoming in member 14) whereas cutouts 20B (FIG. 7) are through-holes through both members 12 and 14.

The anchor 24 may be of the type disclosed in Applicant's co-pending applications Ser. Nos. 08/294,067 and 08/426,715. The anchor is generally indicated at 24 and is of the type which is engaged by an installation tool at its proximal end 26, and having a plurality of longitudinally extending fingers 28 which are adapted to move radially outwardly and engage with the walls of a bore in organic tissue, for example a bore hole in bone. The sutures are generally indicated at 30 and the surgical suture needles are shown at 32.

Figure 6:
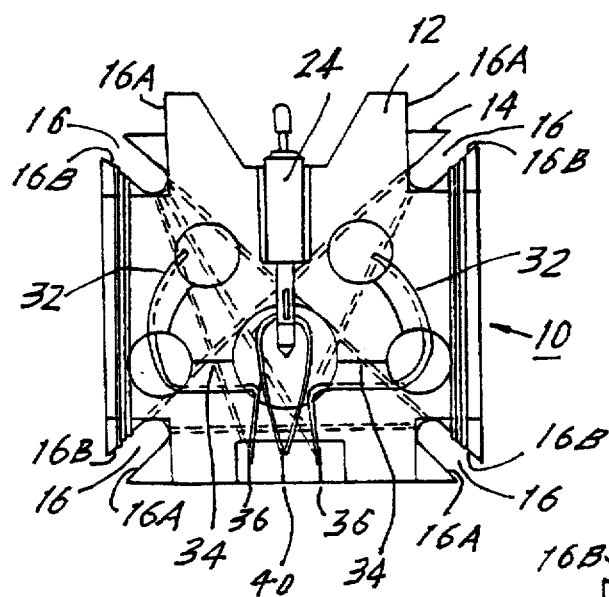
FIG. 6 is a front plan view of the holder according to the present invention with the suture anchor, suture and suture needles held therein.

As shown in the drawing figures, the surgical needles 32 are inserted in the cushioned channels 22 and openings 20 in the member 12, as shown most clearly in FIG. 6. The attached sutures are led through the channels 34 in the member 12, and then through slits 30 provided in the member 14 disposed immediately below a cutout 38 in the member 12. The sutures are then suitably wound, e.g., about the left and right sides of the holder 10 through the cutouts 16 and also across the top and bottom of the holder 10 but only along the backside of the portion 14, thus keeping the opening 18 clear for the insertion of the anchor 24 in the opening 18. Essentially, the sutures can be wound in any convenient manner about the holder 10. Preferably, the length of the sutures is such that they are substantially wound around the holder 10 without substantial looseness. The sutures are fed through a slit 40 provided in the member 14 as shown most clearly in FIGS. 6 and 7. After the sutures are wound about the holder 10, the suture anchor 24 is inserted in the opening 18 in the member 12.

The opening 18 is shaped so as to have a substantially linearly extending portion 18A opening into a circular portion 18B. The portion, 18A is adapted to receive substantially cylindrical portion 24A of the anchor of greater diameter and the circular portion 18B is adapted to receive the portion 24B of the anchor of a smaller cross section and having the engaging fingers 28.

Figure 1:
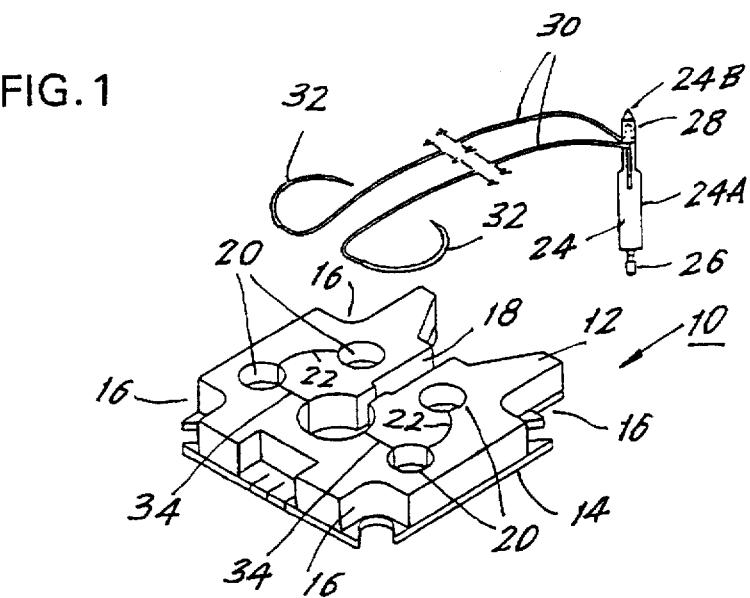
FIG. 1 is a perspective view showing the holder of the present invention and separately, the suture anchor with suture needles attached thereto which is to be held by the holder.
Figure 2:
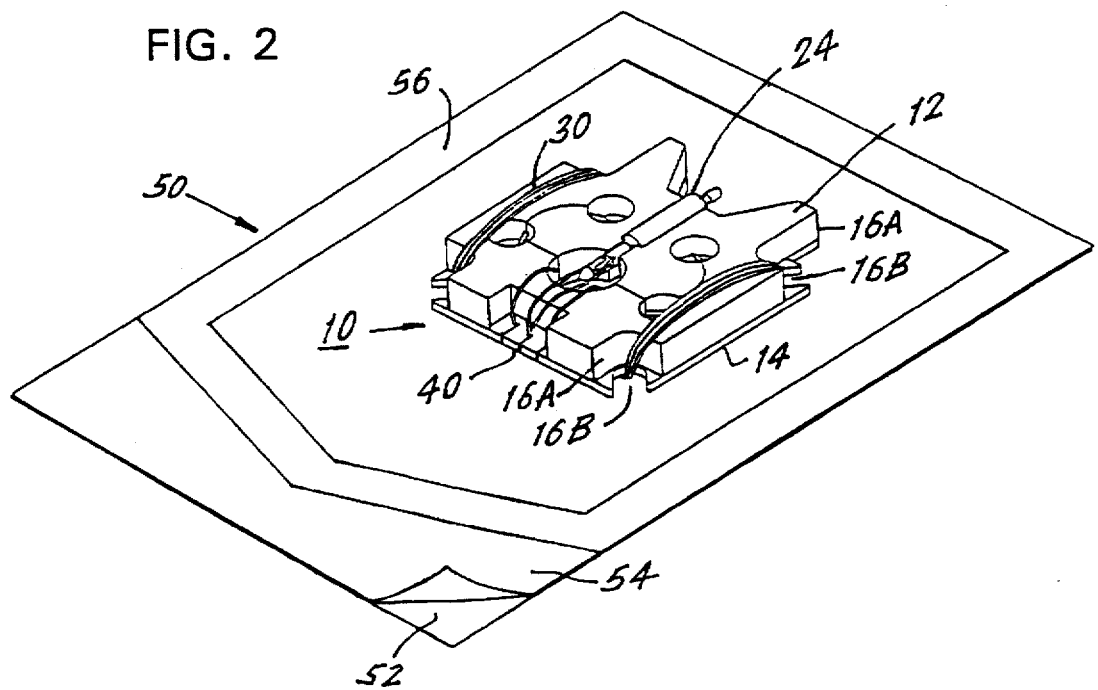
FIG. 2 shows a sterile package for the holder with the suture anchor with sutures and suture needles held therein.
Figure 3:
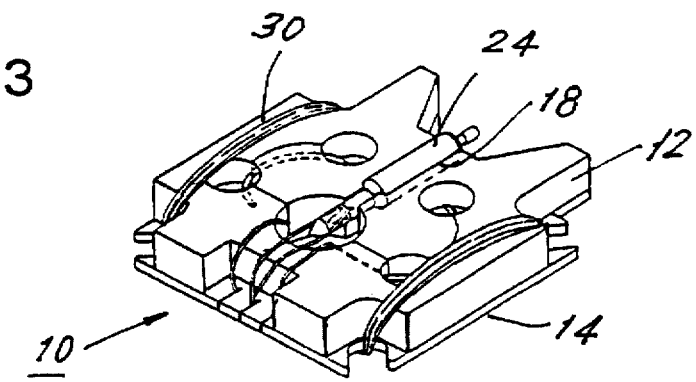
FIG. 3 shows the holder with the suture anchor, suture and suture needles attached thereto.
Figure 4:
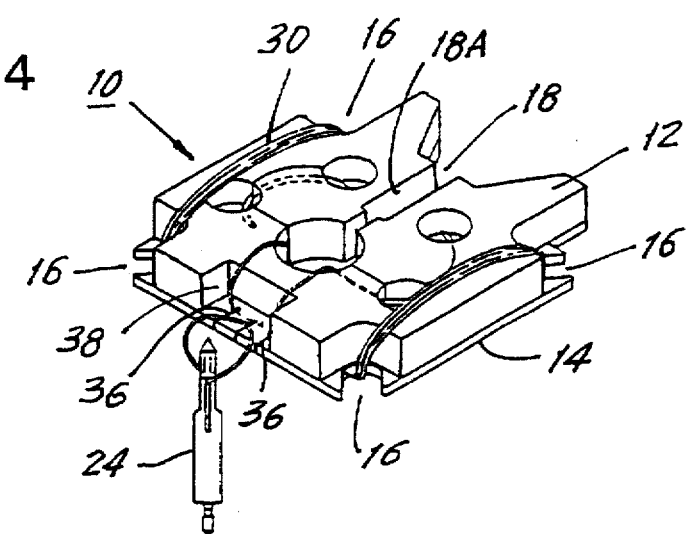
FIG. 4 shows the holder after the suture anchor has been removed from the holder but while the sutures are maintained in a wound state in the holder.
Figure 5:
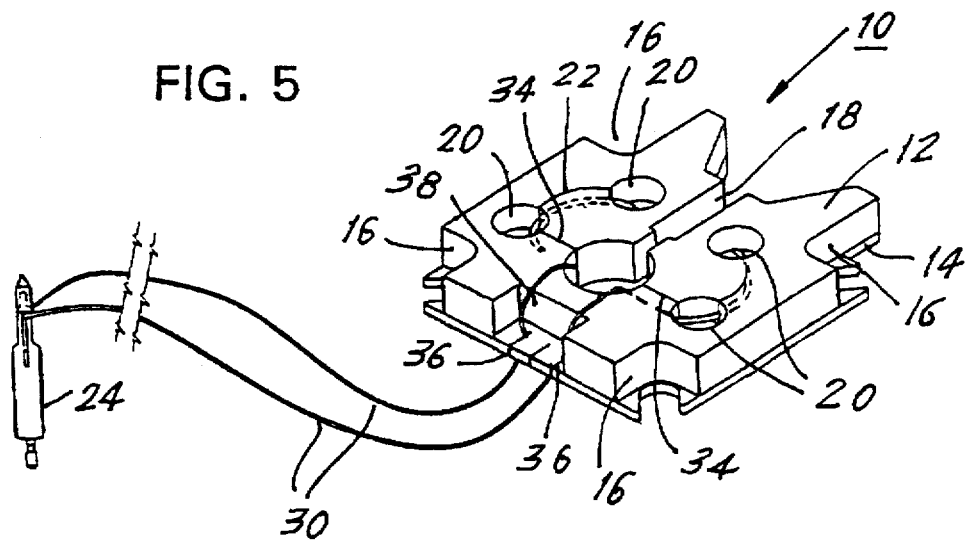
FIG. 5 shows the suture anchor after the bulk of the suture has been unwound from the holder, but while the suture needles remain in position in the holder.

The entire holder with the suture anchor, sutures and suture needles attached thereto is sterilized and disposed in a sterile package 50, as shown in FIG. 2, comprising a first planar member 52 covered by a second transparent planar member 54 which is releasibly adhesively secured to the member 52 through a generally rectangular adhesive strip 56 as known in the art. The member 54 is pulled away from the member 52 as shown in the bottom right-hand corner of FIG. 2, thus releasing the holder 10 from the package 50.

Figure 8:
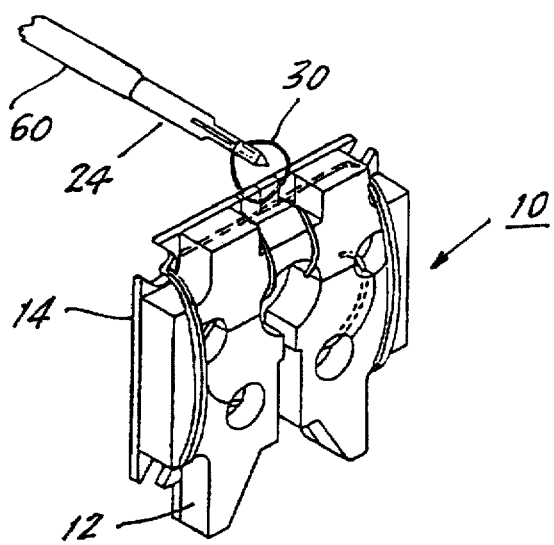
FIG. 8 is a perspective view showing the suture anchor after the suture anchor has been removed from the holder but with the sutures still wound on the holder and with the suture anchor engaged by an installation tool.

In use, the surgeon utilizes an installation tool to install the suture anchor in a bore hole in organic tissue, such as bone. A portion of the installation tool is shown in FIG. 8 at 60, with the suture anchor 24 engaged by the installation tool 60. The anchor 24 can be engaged by the installation tool 60 after the suture anchor is removed from the holder 10, as shown in FIG. 8, or while the suture anchor 24 is still in position in the opening 18 in the holder 10. If the installation tool 60 is attached to the suture anchor 24 after the suture anchor 24 is removed from the holder 10, this is done prior to the removal of the sutures 30 from the slot 40, by which the sutures 30 are frictionally secured to the holder 10. This prevents the sutures 30 from unwinding from the holder 10, and thereby preventing entangling of the sutures 30.

After the suture anchor 24 has been installed in the bore hole at the surgical site, the sutures can be pulled out of the slot 40 in the member 14, and the sutures will unwind from the holder 10. The surgical needles 32 will remain in their receiving cushioning channels in the holder 10 until they are removed by the surgeon for suturing another member to the anchor 24.

The present invention thus provides a convenient holder for a suture anchor with sutures and suture needles attached thereto. The present invention also provides a holder which prevents tangling of the sutures during application and protects the surgical needles and sutures from external contact during the installation of the suture anchor.

The holder of the present invention is light in weight, and, when packaged, provides a sterile cushioned holder for a suture anchor, sutures and surgical needles.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A holder for a suture anchor having a suture coupled to the suture anchor and at least one suture needle attached to the suture, the holder comprising: a planar member of generally rectangular shape having a cutout at each corner of the member about which the suture can be wound, the member having at least one channel formed therein for receiving the surgical needle and a receptacle formed therein for receiving the suture anchor, and further comprising a channel formed in the member for frictionally engaging the suture at a point along the length of the suture close to the suture anchor, thereby allowing the suture anchor to be removed from the holder without causing the suture to unwind from the holder.

2. The holder of claim 1, wherein the cutouts and receptacle for the suture anchor are exposed and a cover is not disposed over the planar member.

3. The holder of claim 1, wherein the member comprises a first planar member having a first thickness at least as thick as a thickness of the anchor, the first planar member joined to a second planar member having a second thickness less than the first thickness.

4. The holder of claim 3, wherein the second planar member is sized so that it overlaps the first member about the periphery of the first member.

5. The holder of claim 1, wherein the planar member has a plurality of cutouts formed therein for receiving the surgical needle.

6. The holder of claim 3, wherein the channel frictionally engaging the suture near the suture anchor is disposed in the second planar member.

7. The holder of claim 6, wherein a cutout is provided in the first planar member above the location in the second planar member where the channel is provided for frictionally engaging the suture near the suture anchor.

8. The holder of claim 1, further comprising a suture anchor disposed in the receptacle in the planar member with a suture coupled to the suture anchor wound around the planar member.

9. The holder of claim 8, further comprising at least one surgical needle attached to the suture, the surgical needle disposed in the channel in the holder.

10. The holder of claim 8, wherein the suture anchor comprises a plurality of longitudinally extending fingers which are adapted to move radially into the wall of a bore hole in which the suture anchor is to be secured.

11. The holder of claim 9, further comprising a sterile package having a pouch for receiving the holder with the suture anchor, suture and at least one surgical needle disposed therein.

12. The holder of claim 11, wherein the package comprises a first layer of material and a second overlying layer of material releasably coupled to the first layer of material.

13. The holder of claim 12, wherein the second layer of material is transparent.

14. The holder of claim 12, wherein the package comprising the first and second layers and the holder with the suture anchor, sutures and surgical needle are sterilized.

15. The holder of claim 12 wherein the first and second layers are releasibly adhesively joined.

16. The holder of claim 1, wherein the planar member comprises a lightweight plastic cushioning foam.

17. The holder of claim 3 wherein the first and second planar members comprise a lightweight plastic cushioning foam.

18. The holder of claim 3, wherein aligned cutouts are provided in the first and second members for facilitating removal of the surgical needle.

19. The holder of claim 8, wherein the suture is wound about at least one side of the planar member between cutouts of the member.

20. The holder of claim 19, wherein the suture is disposed across at least one of top and bottom edges of the planar member along a back surface of the member so as not to interfere with insertion or removal of the suture anchor into the receptacle.

21. The holder of claim 8, wherein the suture is looped through the suture anchor and has two ends, a surgical needle being attached to each end, each surgical needle disposed in a channel in the holder.

22. A package for a holder for a suture anchor having a suture coupled to the suture anchor and at least one suture needle attached to the suture, the package comprising:

a planar member of generally rectangular shape having a cutout at each corner of the member about which the suture is wound, the member having at least one channel formed therein for receiving the surgical needle and a receptacle formed therein for receiving the suture anchor, and further comprising a channel formed in the member for frictionally engaging the suture at a point along the length of the suture close to the suture anchor, thereby allowing the suture anchor to be removed from the holder without causing the suture to unwind from the holder;

a suture anchor in the receptacle;

a suture coupled to the suture anchor wound about the holder;

a surgical needle coupled to the suture and disposed in the channel; and a pouch receiving the holder with the suture anchor, suture and surgical needle disposed thereon.

23. The package of claim 22, wherein the planar member comprises a first planar member having a first thickness at least as thick as a thickness of the anchor, the first planar member joined to a second planar member having a second thickness less than the first thickness.

24. The package of claim 22, wherein the first planar member has a plurality of cutouts formed therein for receiving the surgical needle.

25. The package of claim 23, wherein the channel for frictionally engaging the suture near the suture anchor is disposed in the second planar member.

26. The package of claim 25, wherein a cutout is provided in the first planar member above the location in the second planar member where the channel is provided for frictionally engaging the suture near the suture anchor.

27. The package of claim 22, wherein the suture is looped through the suture anchor and has two ends, a surgical needle being attached to each end, each surgical needle disposed in a channel in the holder.

28. The package of claim 22, wherein the suture anchor comprises a plurality of longitudinally extending fingers which are adapted to move radially into the wall of a bore hole in which the suture anchor is to be secured.

29. The package of claim 22, wherein the pouch comprises a first layer of material and a second overlying layer of material releasibly coupled to the first layer.

30. The package of claim 29, wherein the second layer of material is transparent.

31. The package of claim 29, wherein the pouch comprising the first and second layers and the holder with the suture anchor, sutures and surgical needle are sterilized.

32. The package of claim 22, wherein the cutouts and receptacle for the suture anchor are exposed and a cover is not disposed over the planar member.

33. The package of claim 29, wherein the first and second layers are releasibly adhesively joined.

34. The package of claim 22, wherein the planar member comprises a lightweight plastic cushioning foam.

35. The package of claim 23, wherein the first and second planar members comprise a lightweight plastic cushioning foam.

36. The package of claim 23, wherein aligned cutouts are provided in the first and second members for facilitating removal of the surgical needle.

37. A holder for a suture anchor having a suture coupled to the suture anchor and at least one suture needle attached to the suture, the holder comprising: a member having a surface having a substantially planar portion having a cutout at each corner of the member about which the suture can be wound, the member having at least one channel formed therein for receiving the surgical needle and a receptacle formed therein for receiving the suture anchor, and further wherein the suture is frictionally engaged by the holder at a point along the length of the suture close to the suture anchor, thereby allowing the suture anchor to be removed from the holder without causing the suture to unwind from the holder, the cutouts and receptacle for the suture anchor being exposed and a cover not being disposed over the member.

38. The holder of claim 37, further comprising a suture anchor disposed in the receptacle in the member with a suture coupled to the suture anchor wound around the member.

39. The holder of claim 38, further comprising at least one surgical needle attached to the suture, the surgical needle disposed in the channel in the holder.

40. The holder of claim 38, wherein the suture anchor comprises a plurality of longitudinally extending fingers which are adapted to move radially into the wall of a bore hole in which the suture anchor is to be secured.

41. The holder of claim 38, further comprising a sterile package having a pouch for receiving the holder with the suture anchor, suture and at least one surgical needle disposed therein.

42. The holder of claim 37, wherein the member comprises a lightweight plastic cushioning foam.

43. The holder of claim 38, wherein the suture is wound about at least one side of the planar member between cutouts of the member.

44. The holder of claim 43, wherein the suture is disposed across at least one of top and bottom edges of the planar member along a back surface of the member so as not to interfere with insertion or removal of the suture anchor into the receptacle.

45. The holder of claim 38, wherein the suture is looped through the suture anchor and has two ends, a surgical needle being attached to each end, each surgical needle disposed in a channel in the holder.

46. A holder for a suture anchor having a suture coupled to the suture anchor and at least one suture needle attached to the suture, the holder comprising:

a member having a surface having a substantially planar portion having a cutout at each corner of the member about which the suture can be wound, the member having at least one channel formed therein for receiving the surgical needle and a receptacle formed therein for receiving the suture anchor and further wherein the suture is wound about at least one side of the member between the cutouts of the member.

47. The holder of claim 46 wherein the suture is disposed across at least one of top and bottom edges of the planar member along a back surface of the member so as not to interfere with insertion or removal of the suture anchor into the receptacle.

* * * * *